United States Patent [19]

Gustavson et al.

[11] Patent Number: 5,108,435
[45] Date of Patent: Apr. 28, 1992

[54] CAST BONE INGROWTH SURFACE

[75] Inventors: Larry J. Gustavson, Dover; Melvin M. Schwartz, Jersey City, both of N.J.

[73] Assignee: Pfizer Hospital Products Group, Inc., New York, N.Y.

[21] Appl. No.: 630,420

[22] Filed: Nov. 19, 1990

Related U.S. Application Data

[63] Continuation of Ser. No. 413,936, Sep. 28, 1989, abandoned.

[51] Int. Cl.⁵ .............................................. A61F 2/28
[52] U.S. Cl. ...................................... 623/16; 623/66; 623/20; 623/11
[58] Field of Search ................................ 623/16–18, 623/20, 22–23, 66, 11

[56] References Cited

U.S. PATENT DOCUMENTS

| | | | |
|---|---|---|---|
| 3,576,074 | 4/1971 | Gault et al. | |
| 3,605,123 | 9/1971 | Hahn | 628/16 |
| 3,710,789 | 1/1973 | Ersek | 128/92 |
| 3,715,763 | 2/1973 | Link | 623/20 |
| 3,855,638 | 12/1974 | Pilliar | 623/16 |
| 3,905,777 | 9/1975 | Lacroix | 29/183.5 |
| 3,906,550 | 9/1975 | Rostoker et al. | 623/16 |
| 4,089,071 | 5/1978 | Kalnberz et al. | 623/16 |
| 4,209,861 | 7/1980 | Walker et al. | 623/20 |
| 4,261,063 | 4/1981 | Blanquaert | 623/18 |
| 4,355,428 | 10/1982 | Deloison et al. | 623/18 |
| 4,550,448 | 11/1985 | Kenna | 623/16 |
| 4,623,349 | 11/1986 | Lord | 623/18 |
| 4,636,219 | 1/1987 | Pratt et al. | 623/22 |
| 4,644,942 | 2/1987 | Sump | 623/16 |
| 4,722,870 | 2/1988 | White | 428/621 |
| 4,863,474 | 9/1989 | Brown et al. | 623/16 |

FOREIGN PATENT DOCUMENTS 0230006 12/1986 European Pat. Off. .
645265 9/1984 Switzerland .
1316809 5/1973 United Kingdom .

OTHER PUBLICATIONS

Zimmer, 1983 Catalog Supplement, 1983, p. 53.
Translation of EP 0230 006 A1.
Page from 1978 Howmedica Catalog.
1981 Howmedica Custom Catalog.
Howmedica Drawing No. B-2920-3-XXX.

Primary Examiner—David Isabella
Assistant Examiner—Gina M. Gualtieri
Attorney, Agent, or Firm—Richardson, Peter C.; Lawrence C. Akers; Raymond W. Augustin

[57] ABSTRACT

A prosthetic part for use as an orthopaedic implant has a cast metal base member and a tissue ingrowth surface spaced outwardly therefrom. The tissue ingrowth surface is in the form of a cast metal lattice element which covers at least a part of the outer surface of the base member. The cast metal lattice element is cast simultaneously and integrally with the base member from the same metal. This metal may be any well known castable material for orthopaedic implants such as Vitallium or titanium. The lattice element is in the form of a grid-like mesh which includes spaced members cast integrally with the wire mesh and the base member to space the lattice element a predetermined distance above the prosthesis surface. An investment casting technique wherein a meltable material is coated with a ceramic casting shell is utilized to produce the integrally cast orthopaedic implant and tissue ingrowth surface.

7 Claims, 4 Drawing Sheets

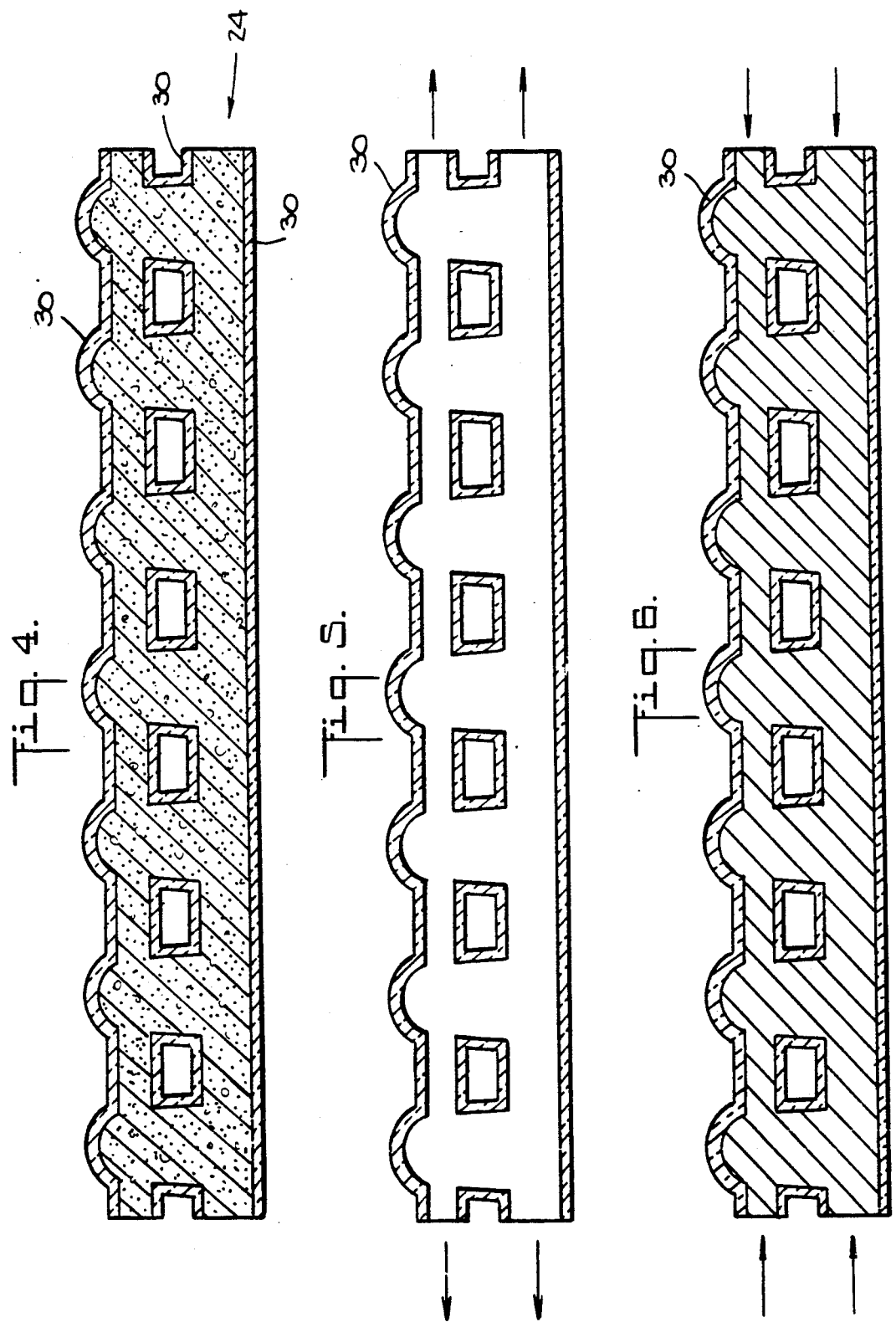

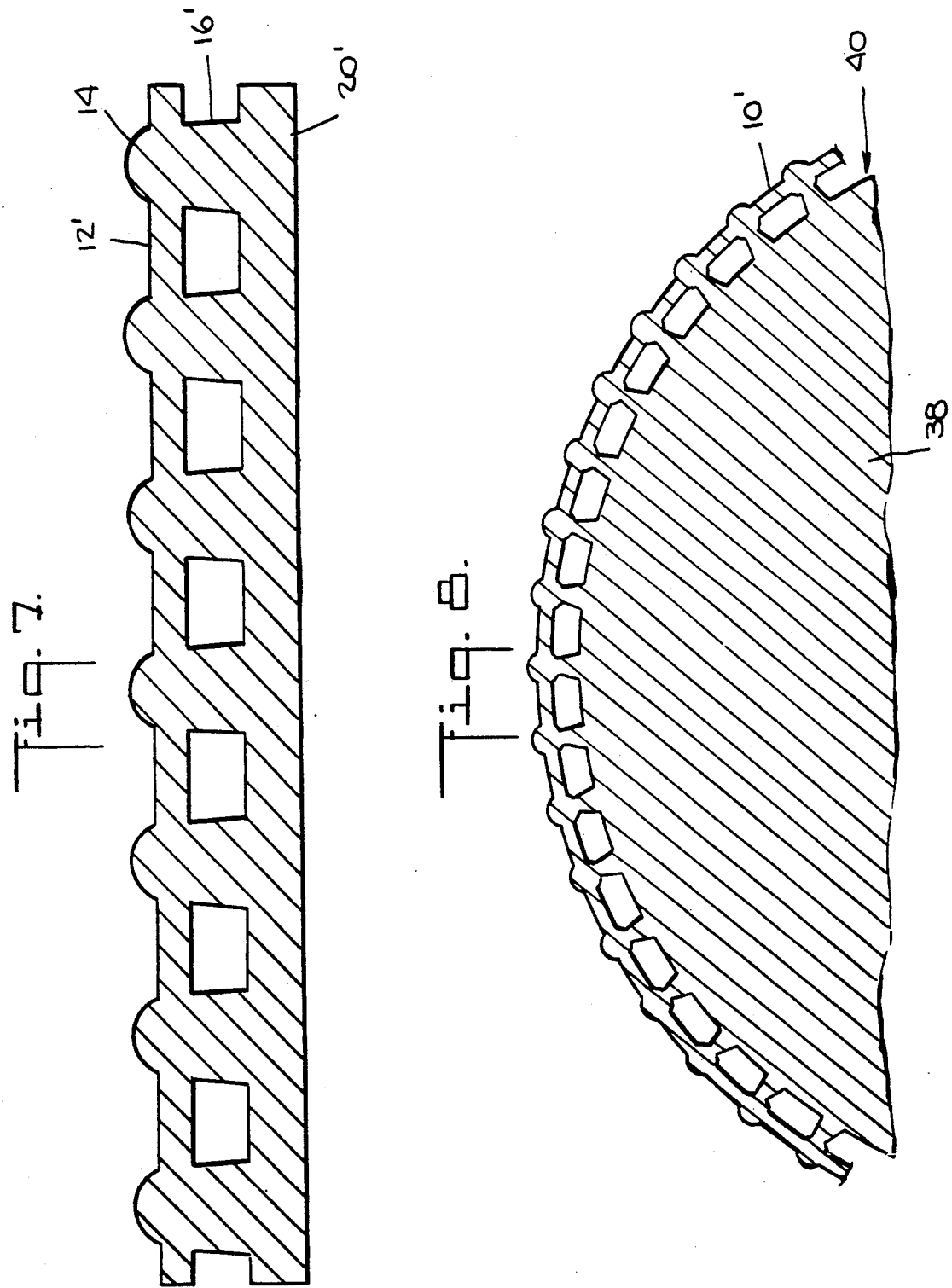

CAST BONE INGROWTH SURFACE

This is a continuation of application Ser. No. 413,936, filed on Sep. 28, 1989, now abandoned.

BACKGROUND OF THE INVENTION

1. Field of the Invention

This invention relates to an integrally cast tissue ingrowth surface apparatus and a method for casting the same. More particularly, the invention relates to an integrally cast bone or tissue ingrowth surface in a cast metal orthopaedic prosthesis.

2. Description of the Prior Art

Investment casting or the "lost wax process" has been used for over 50 years in the production of medical and dental implants. The process derives its name from the investment of wax or other suitable mold material and ceramics used to produce an expendable mold for casting.

The investment casting process used to produce orthopaedic implants is common to the industry and is used to produce implants from Co—Cr—Mo ("Vitallium") alloys as well as titanium alloys and stainless steels. Being well suited to the manufacture of the complex shapes typical of many implant designs, investment casting is used extensively to produce components for bone implants or total joint prostheses such as knees and hips.

These prostheses typically consist of metallic and polymeric components where the metallic components rest against bone on one side of the joint and bear against the polymeric component on the other. The bearing surfaces of a total joint have evolved in design to closely mimic the movement of the natural joint, while the bone contacting sides have evolved to assure improved fixation of the implanted prosthesis with the surrounding bone.

Until recently, total joint prostheses were designed for implantation with bone cement. For example, a polymethylmethacrylate (PMMA) grouting agent may be used to secure the prosthesis component against the surrounding bone. Implant surfaces contacting the cement were either cast smooth or with a two dimensional texture intended to improve fixation with the PMMA grout.

Recurrent loosening of these cemented implants, due to loss of support in underlying bone, lead to the development of prostheses with three dimensionally porous fixation surfaces which could be used without the PMMA bone cement. These prostheses instead rely on fixation via the ingrowth of bone or other connective tissue directly into the prosthesis surfaces, thereby anchoring the prosthesis to the bone.

These three dimensionally textured surfaces are created by bonding a suitable network of material, usually metal of the same composition as the implant, onto the implant's fixation surfaces to create a porous coating. The nature of the porosity present in the coating is generally a direct function of the materials and methods used to produce the coating.

Porous surfaces have been created by plasma spraying (U.S. Pat. No. 3,605,123) of fine metallic particles, or by sintering a loosely packed coating of metallic particles (U.S. Pat. No. 4,550,448, British Patent 1316809), or by diffusion bonding kinked fiber metal pads (U.S. Pat. No. 3,906,550), or overlapping mesh (U.S. Pat. No. 4,636,219).

In another concept, integrally formed ceramic filled porous areas are formed on the prosthesis. U.S. Pat. No. 4,722,870 discloses a method for investment casting a composite implant which produces a porous metal structure filled with a ceramic (hydroxyapatite). However, this structure cannot be accurately controlled nor can it be spaced a predetermined distance above the outer surface of the implant.

Other U.S. patents describe mesh surfaces welded to the implant. Such a mesh is shown in U.S. Pat. No. 3,905,777 to Lacroix, U.S. Pat. No. 4,089,071 to Kalnberz et al, U.S. Pat. No. 4,261,063 to Blanquaert and U.S. Pat. No. 4,636,219 to Pratt et al. None of these surfaces are integrally cast with the prosthesis.

Each of the aforementioned methods for producing a porous ingrowth surface entails applying a porous network onto the surface of a metallic implant and bonding that network through the application of heat. Plasma spraying employs super heated gases to melt the metal particles to be sprayed. Sintering develops interparticle bonds in a porous coating by exposing the coating and implant metal to temperatures approaching their melting point, while diffusion bonding employs heat and pressure to promote atomic diffusion at the coating implant interface.

Each of these methods has its limitations. Plasma spraying cannot be adequately controlled to achieve a uniform interconnected pore structure in the coating. The temperatures required for sintering have a deleterious effect on the implant materials strength, and diffusion bonding develops variations in pore structure and bond quality due to variations in pressure distribution during the coating process. Each of the processes is limited in its achievable pore size by the loss in coating strength which occurs as coating porosity increases.

Particulate porous coatings are also inherently accompanied by a dramatic increase in surface area of metal exposed to body fluids, increasing proportionally the corrosion products which are released after implantation.

Clinical reports exist of metal particles becoming loose from bonded coatings or fiber pads becoming detached on revision surgery. Furthermore, bonded coatings inherently develop stress concentrating surface notches at the coating - substrate interface which limit the locations a porous coating can be placed due to strength considerations. By their very nature, bonded coatings require the use of a secondary manufacturing process to affix the coating to the implant surfaces. These processes increase manufacturing costs through added labor, materials, tooling and fixturing.

SUMMARY OF THE INVENTION

It is an object of this invention to provide a biocompatible interconnected porous surface on prostheses for purposes of improved implant fixation, which is an integral part of the prosthesis, being produced by casting a three dimensional grid-like or lattice structure directly onto the prosthesis surfaces.

A further object is to provide a one step process for creating porous surfaces on prostheses which does not require thermal processing, which may be detrimental to the substrate materials mechanical properties, and does not involve the expense of a secondary coating process.

A further object is to allow an implant's porous surface to be precisely controlled relative to pore shape, pore size, pore size distribution, substrate bonding and coating stress concentrations.

These and related objects are achieved in the present invention by an apparatus having a cast metal base member having an outer surface designed to rest against a bone after implantation. A tissue ingrowth surface in the form of a cast metal lattice element composed of a grid-like element spaced a predetermined distance away from the base member outer surface is integrally cast with the base member, from the same metal, over at least a part of the outer surface thereof. The metal utilized may be "Vitallium", titanium alloy or other suitable biocompatible metallic alloys.

Either the tissue ingrowth surface element or the cast metal base member may include spacer elements to space the lattice element a predetermined distance above the outer surface of the base member. If the lattice element is in the form of a square or rectangular grid this permits tissue to grow over and under the cross members of the lattice element. The lattice element may be in the form of a wire mesh integrally cast with the base member and spaced therefrom.

An investment casting technique, wherein a meltable material is coated with a ceramic casting shell may be utilized to cast the tissue ingrowth surface and the base member of the metal orthopaedic implant. As is well known, the meltable material, such as wax, has a melting point lower than the ceramic. A pattern is formed corresponding to the orthopaedic implant from the meltable material. The lattice element is then also formed from the meltable material in any well known manner such as utilizing a two-part die to mold the wax or other meltable material. Once the lattice element is formed, it is joined to the pattern corresponding to the orthopaedic implant. This may be done by using a solvent which melts part of the materials to be joined, thereby allowing an integral, one-piece pattern to be formed from the meltable material after joining. The joined combination of the pattern and the lattice is then coated with a ceramic slurry to form a casting shell in a well known manner. The meltable material is then removed from the casting shell by heating. As is well known, the empty casting shell is filled with molten metal and allowed to cool, thereby forming a one piece casting in the form of the pattern corresponding to the orthopaedic implant with the lattice integrally cast therewith. While wax is preferably used as the meltable material, other materials such as polystyrene may also be used. In order to achieve any proper spacing, spacers made of the meltable material are inserted between the lattice and the pattern corresponding to the orthopaedic implant during the joining operation. Alternately, the spacers may be formed as either part of the lattice element or the orthopaedic implant pattern. Usually this joining operation involves a solvent which causes the meltable material to partially liquify and therefore allows the various parts to be made integral with one another.

It should be noted that the bone ingrowth surface can also be utilized in cemented application, since the cast surface will produce better adhesion between the cement and the prosthesis.

These and other objects and features of the present invention will become apparent from the following detailed description considered in connection with the accompanying drawings, which disclose several embodiments of the invention. It is to be understood that the drawings are to used for the purposes of illustration only, and not as a definition of the limits of the invention.

BRIEF DESCRIPTION OF THE DRAWINGS

In the drawings, wherein similar reference characters denote similar elements throughout the several views:

FIG. 4 is an enlarged cross-sectional view of the joined lattice element and the orthopaedic implant of FIG. 3 covered by a casting shell;

FIG. 5 is a view of FIG. 4 after removal of the meltable material by heating;

FIG. 6 is a view of FIG. 5 after molten base metal has been introduced into the casting shell of FIG. 5;

FIG. 7 is a cross-sectional view of the integrally cast orthopaedic implant and lattice element of the present invention; and FIG. 8 is a partial cross-sectional view of a femoral component of a total hip prosthesis, having the tissue ingrowth surface in the form of the lattice element integrally cast on the outer surface thereof.

DESCRIPTION OF THE PREFERRED EMBODIMENTS

Figure 1:
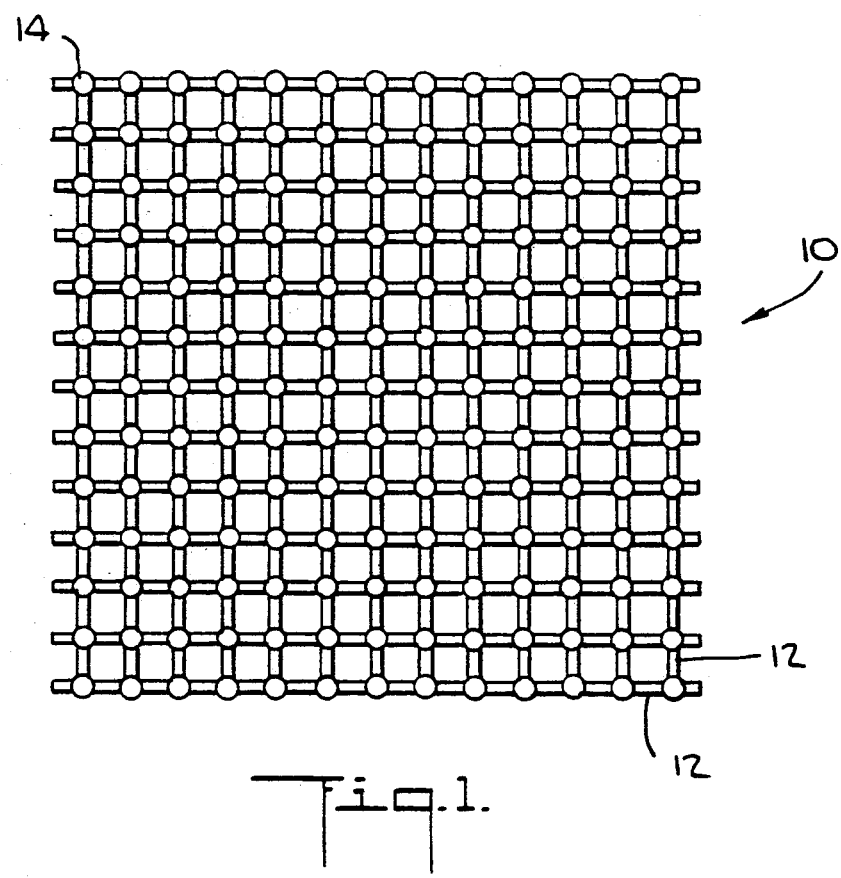
FIG. 1 is a plan view of the lattice element of the present invention in the form of a meltable material.
Figure 2:
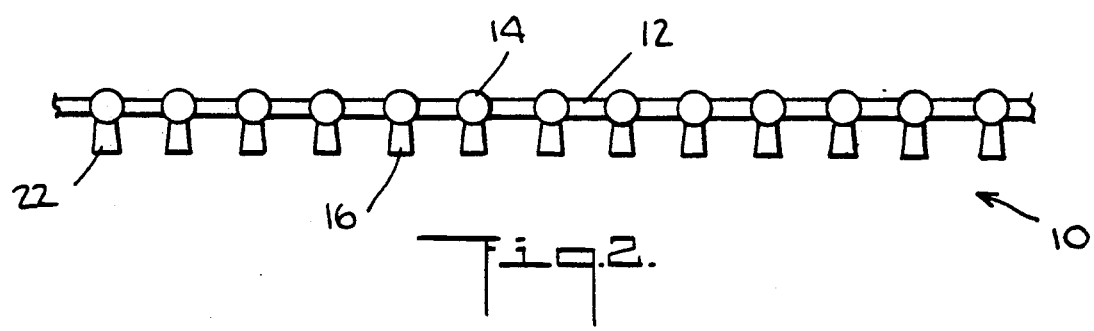
FIG. 2 is an elevation view of the lattice element of FIG. 1.
Figure 3:
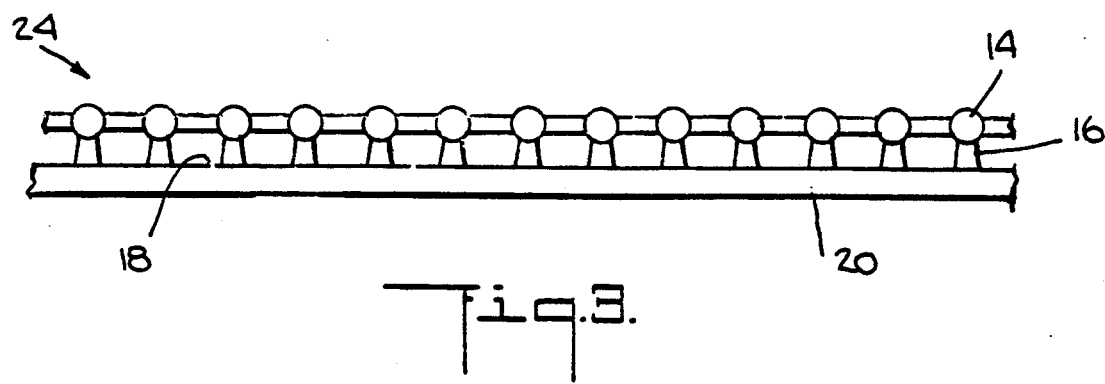
FIG. 3 is an elevation view of the lattice element of FIG. 1 joined to a pattern of an orthopaedic implant also made of meltable material.

Referring to FIGS. 1-3, there is shown the tissue ingrowth surface of the present invention, generally denoted as 10, in the form of a lattice element or grid-like mesh made out of a meltable material. Preferably, the meltable material is wax although polystyrene may also be used. Lattice element 10 may be molded with a two-piece die in any well known manner.

Lattice element 10 may be in the form of a uniform grid of crossing members 12 intersecting at protrusions 14. Preferably, each protrusions 14 includes a spacer member 16 extending downwardly therefrom. Spacers 16 serve to space connecting members 12 a predetermined distance from the outer surface of any suitable orthopaedic implant.

As stated above, wax or plastic lattice element 10 is produced by injection molding in a split die (not shown) to form a grid-like three dimensional network. After cooling, lattice element 10 is removed from the molding apparatus and is substantially as shown in FIGS. 1 and 2. Typically the cross-members 12 are 0.020" in diameter and the spherical protrusions 14 are 0.040" in diameter. The spacers 16 may be of any desirable length, typically 0.060".

Referring to FIG. 3, it can be seen that lattice element 10 may be joined to the outer surface 18 of a pattern corresponding to the orthopaedic implant 20. Orthopaedic implant 20, having a body also made from a meltable material such as wax or polystyrene. The joining operation may be accomplished by placing a glue or solvent on the outer surface 18 of the orthopaedic implant 20, which causes local melting or liquification of the meltable pattern. By placing the base 22 of spacer 16 of lattice element 10 on to the partially liquified areas of surface 18, a slight melting or liquification of base 22 of spacer 16 occurs. Upon evaporation of the solvent and the subsequent hardening of the meltable material, an integrally joined pattern, generally denoted as 24, is formed. Of course, the glue or solvent may be applied to base 22 of spacer 16, rather than to top surface 18 of orthopaedic implant pattern 20, with the same result. While it is intended that each spacer 16 be integrally joined with the pattern 20, it can be seen that even if an inadequate bond is formed on a few spacers 16, sufficient attachment strength will still be developed between the final cast ingrowth surface and the implant body. It has been found that Testor's model cement acts as an adequate solvent when the lattice element is made of a Yates JW2 wax and the orthopaedic implant pattern is made from a Yates PX-12 wax. All of these materials are readily available and are well known in the investment casting art.

After the one piece pattern 24 has been formed, the investment casting process proceeds with the pattern 24 being coated with a slurry of colloidal silica binder of the type including refractory powders of zirconia, alumina and silica. The first coat of the slurry used to form the shell in the investment casting process is critical. The first coat should have a viscosity of 12-14 seconds measured with a #4 Zahn cup. A preferred slurry for this first coat is a colloidal silica binder (such as Du-Pont's 30% colloidal binder) base with refractory zirconia and silica flours. The viscosity can be varied by adding more or less binder. The dip pattern must be designed to make sure that one-piece pattern 24 is completely and evenly coated. Pattern 24 must be vibrated while draining, with air lightly blown over the lattice pattern to break up any air bubbles to prevent the slurry from bridging the grid openings. With care, it has been found that this technique can be used to produce grid openings of 0.020" and above. With the use of the injection molding process for the meltable material, various pattern shapes, such as square, rectangular or triangular, may be used for the tissue ingrowth surface. With this process, the shapes and sizes can be accurately controlled. Thus, various pattern shapes can be fabricated to fit specific implant designs. Furthermore, the potential variability of pore spacing would allow for the use of bone inductive coatings or fillers such as hydroxyapatite to facilitate tissue or bone ingrowth as well as more precise engineering and control of pore structures as required for improved osseo integration or vascularization.

The process for the formation of shell 30 is shown in FIGS. 4-7 with, after the initial coat is allowed to dry, additional slurry coats being applied in the well known manner forming the ceramic shell 30 as shown in FIG. 4. Note that the usual stucco is not applied after the first coat, but is applied after application of the backup coats. The combined pattern 24 made of meltable material is then removed from the shell by heating in a well known manner. This results in a void being formed within a shell 30 as shown in FIG. 5. Molten metal, such as "Vitallium" alloy or titanium is introduced into the void, as shown in FIG. 6, and allowed to cool. Of course, it is well known that in order to cast titanium, special foundry practices must be followed. If this is done, the cast ingrowth surface of the present invention can be produced.

After removal of shell 30, the integral one-piece casting is shown in cross-section, in FIG. 7. As, can be seen, connecting elements 12' forming lattice ', the protrusion, 14', a spacer 16', and the orthopaedic implant pattern 20' having upper surface ∼' are now a one-piece casting of for example of Vitallium or titanium.

Referring to FIG. 8, it can be seen that the integral cast lattice element forming a tissue ingrowth surface can be easily produced on the outside of a femoral component of a hip prosthesis. This is accomplished by utilizing a formulation of wax or polystyrene which is suitably flexible and can be wrapped around the outer surface 40 of the hip prosthesis 38. Such a wax is Yates JW-2 wax.

Figure 9:
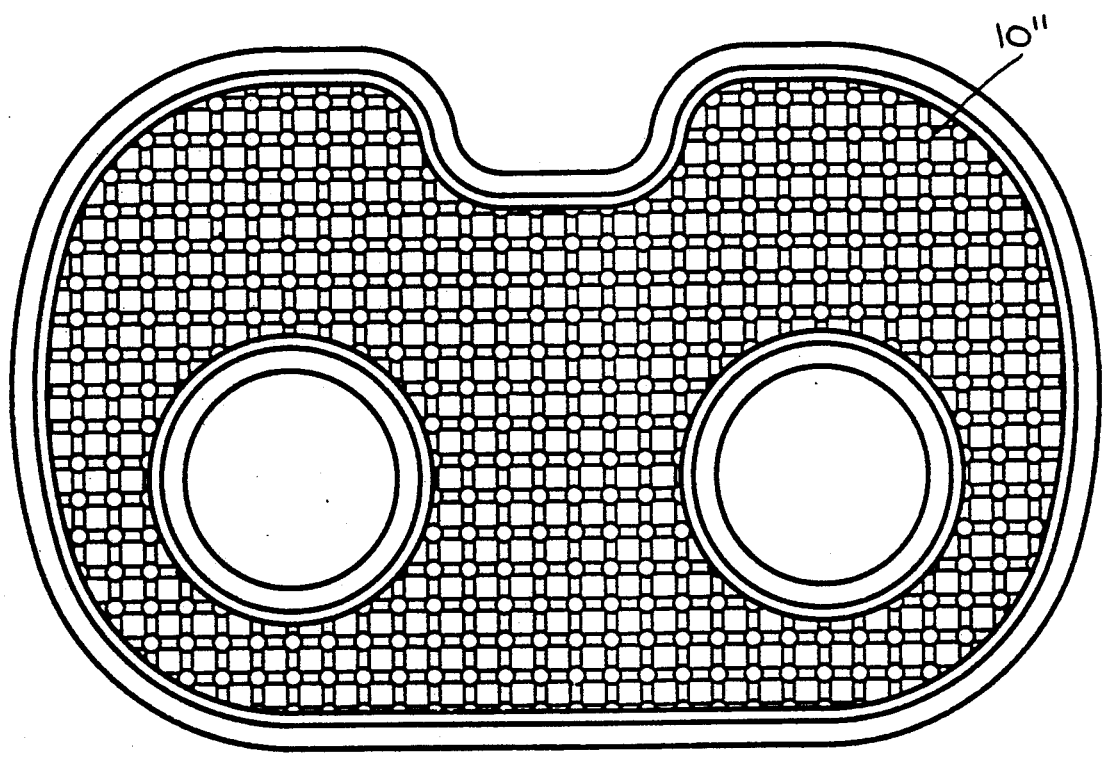
FIG. 9 is a finished tibial plate with the tissue ingrowth surface of the invention cast thereon.

Referring to FIG. 9, there is shown a tibial component of a knee prosthesis in which the bottom surface of the tibial plate (the surface which comes in contact with the top surface of the tibia after implantation) includes the lattice element 10" thereby forming an ideal tissue ingrowth surface.

While several examples of the present invention have been described, it is obvious that many changes and modifications may be made thereunto, without departing the spirit and scope of the invention.

We claim:

1. An orthopaedic implant comprising:
   a cast metal base member having an outer surface;
   a plurality of generally cylindrical spacer elements integrally cast with said base member from the same metal as said base member and each spacer element extending the same predetermined distance outwardly from said outer surface thereof; and
   a metal attachment element integrally cast with said plurality of spacer elements, said attachment element having connecting elements for contact with a bone extending between said spacer elements to allow attachment to bone to occur between an underside of said connecting elements and said outer surface of said base member, all of said connecting elements extending in the same plane.

2. The orthopaedic implant as set forth in claim 1 wherein said metal is a cobalt-chrome alloy.

3. The orthopaedic implant as set forth in claim 1 wherein said metal is cobalt-chrome.

4. The orthopaedic implant as set forth in claim 1 wherein said connecting elements define openings between the outer surface of the cast metal base member to allow for tissue ingrowth.

5. The orthopaedic implant as set forth in claim 1 wherein said connecting elements define openings between the outer surface of the cast metal base member to allow for the introduction of bone cement.

6. The orthopaedic implant as set forth in claim 1 wherein said metal attachment element is in the form of a grid-like mesh comprised of a multiplicity of cross-members.

7. The orthopaedic implant as set forth in claim 1 wherein said connecting elements form a grid-like mesh having openings of at least 0.020 inches.

* * * * *

UNITED STATES PATENT AND TRADEMARK OFFICE
CERTIFICATE OF CORRECTION

PATENT NO. : 5,108,435
DATED : April 28, 1992
INVENTOR(S) : Gustavson et al.

It is certified that error appears in the above-identified patent and that said Letters Patent is hereby corrected as shown below:

On the Title Page, item [22], "Nov." should read --Dec.--

Signed and Sealed this

Twenty-first Day of December, 1999

Attest:

Q. TODD DICKINSON

*Attesting Officer*    *Acting Commissioner of Patents and Trademarks*